United States Patent [19]
Simborg et al.

[11] Patent Number: 5,950,168
[45] Date of Patent: Sep. 7, 1999

[54] COLLAPSIBLE FLOWSHEET FOR DISPLAYING PATIENT INFORMATION IN AN ELECTRONIC MEDICAL RECORD

[75] Inventors: Donald W. Simborg, Greenbrae; Robert J. Barcklay, Berkeley; Paul H. Lipkin, Piedmont, all of Calif.

[73] Assignee: KnowMed Systems, Berkeley, Calif.

[21] Appl. No.: 08/769,096

[22] Filed: Dec. 18, 1996

[51] Int. Cl.⁶ .................................................. G06F 17/30
[52] U.S. Cl. .............................. 705/3; 345/356; 707/104
[58] Field of Search ........................... 705/2, 3; 706/924; 707/104; 345/334, 353, 356

[56] References Cited

U.S. PATENT DOCUMENTS

| | | | |
|---|---|---|---|
| 4,878,175 | 10/1989 | Norden-Paul et al. | 705/2 |
| 5,072,383 | 12/1991 | Brimm et al. | 705/2 |
| 5,115,501 | 5/1992 | Kerr | 707/9 |
| 5,148,366 | 9/1992 | Buchanan et al. | 707/531 |
| 5,208,907 | 5/1993 | Shelton et al. | 707/505 |
| 5,262,943 | 11/1993 | Thibado et al. | 600/300 |
| 5,267,155 | 11/1993 | Buchanan et al. | 707/540 |
| 5,327,341 | 7/1994 | Whalen et al. | 705/3 |
| 5,361,202 | 11/1994 | Doue | 705/3 |
| 5,450,538 | 9/1995 | Glaser et al. | 707/508 |
| 5,473,536 | 12/1995 | Wimmer | 364/400 |
| 5,495,567 | 2/1996 | Iizawa et al. | 345/334 |
| 5,530,942 | 6/1996 | Tzou et al. | 707/512 |
| 5,535,321 | 7/1996 | Massaro et al. | 345/337 |
| 5,544,285 | 8/1996 | Glaser et al. | 707/506 |
| 5,546,580 | 8/1996 | Seliger et al. | 707/104 |
| 5,551,022 | 8/1996 | Tariq et al. | 707/104 |
| 5,559,945 | 9/1996 | Beaudet et al. | 345/353 |
| 5,561,793 | 10/1996 | Bennett et al. | 707/201 |
| 5,581,685 | 12/1996 | Sakurai | 345/353 |
| 5,588,107 | 12/1996 | Bowden et al. | 345/356 |
| 5,615,112 | 3/1997 | Liu Sheng et al. | 707/104 |
| 5,621,905 | 4/1997 | Jewson et al. | 345/353 |
| 5,664,109 | 9/1997 | Johnson et al. | 705/2 |
| 5,682,526 | 10/1997 | Smokoff et al. | 707/104 |
| 5,701,137 | 12/1997 | Kiernan et al. | 345/356 |
| 5,760,776 | 6/1998 | McGurrin et al. | 345/353 |
| 5,772,585 | 6/1998 | Lavin et al. | 600/300 |

*Primary Examiner*—Eric W. Stamber
*Attorney, Agent, or Firm*—Townsend & Townsend & Crew LLP

[57] ABSTRACT

In one embodiment, a user interface presents patient data on a computer display to a health care provider as a flowsheet including an array of category labels with indications of whether the category is in a collapsed state or an expanded state, the collapsed state being a state wherein data items in that category which are tagged as being hidden items are not displayed and the expanded state being a state wherein data items in that category which are tagged as being hidden items are displayed. Also included is a hierarchical structure of data items associated with at least some of the category labels, wherein parent data items are data items which are above other data items in the hierarchical structure and child data items are data items which are below other data items in the hierarchical structure. For each parent data item, a zipper indicator is provided to indicate whether the parent data item is in a zipped state or an unzipped state, the zipped state being a state where child data items are not displayed below the parent data item and the unzipped state being a state where child data items are displayed below the parent data item. In addition, the columns corresponding to patient encounters can also be collapsed and expanded.

6 Claims, 4 Drawing Sheets

| | | 10/29/96 Dr. Walters Medicine | 06/08/96 Dr. Walters Medicine | 04/22/96 Dr. Walters Medicine | 01/13/96 Dr. Walters Medicine |
|---|---|---|---|---|---|
| Problem | Asthma | | Doing better... | Pt learned s... | Pt with long... |
| | Lungs | | | | normal che... |
| | Wheezes | | none | apex, 1 + | |
| | DOE | —24 | 1 flight | 1 flight | |
| | Heart | | | normal | normal |
| | Right Breast carcinoma | | | | |
| | Megace | | | | |
| | Radiation therapy | | | | |
| | S/P Lumpectomy R Breat 4/14/93 | | | | |
| | S/P Excision biopsy R breat & R axillar | | | | |
| | S/P resection R axillary mass 9/29/95 | | | | |
| | Vital signs | | | | |
| | Weight(kg) | | 84.5 | 84.7 | 84.3 |
| Procedure | Chest PA and Lateral | | Normal ch | | |
| Therapy | Beclovent | | 2 puffs q4-6 | 2 puffs q4-6 | 2 puffs q4-6 |
| | Seldane | | 60 mg bid | 60 mg bid | 60 mg bid |
| | *AC Regimen* | | | | |
| | *Tamoxifen* | | | | |
| Text Note | Encounter Note | | | | |

Logoff | Today | Routers | Medline | Administration | Other
10:00 AM Cynthia Gardner, 56 — Alerts: None
Patient | VisitReason: Follow-up Breast Cancer — Allergies: Tofranil KnowMed Systems Physician Workstation

FIG. 3

KnowMed Systems Physician Workstation

Logoff | Today | Routers | Medline | Administration | Other

10:00 AM  Cynthia Gardner, 56  ▶ Alerts: None

Patient  VisitReason: Follow-up Breast Cancer  Allergies: Tofranil

| Problem | Therapy | | 10/29/96 Dr. Walters Medicine | 06/08/96 Dr. Walters Medicine | 04/22/96 Dr. Walters Medicine | 01/13/96 Dr. Walters Medicine |
|---|---|---|---|---|---|---|
| Procedure | Visit | | | | | |
| Angina pectoris | | ▶ | | | | |
| ? Blood Pressure | | | | 120/80 | 130/85 | 112/78 |
| ? Weight | | | | | | |
| ? Heart | | | | | normal | normal |
| ? Lungs | | ▶ | | | | normal che... |
| Wheezes | | | | none | apex, 1 + | |
| DOE | | | | 1 flight | 1 flight | |
| ? TSH | | | today | | | |
| ? Chem 22 | | | today | | | |
| ? Stress EKG | | | 1 week | | | |
| ? CBC | | | today | | | |
| ? Nitroglycerin | | | 6.4 mg prn | | | |
| ? Isordil | | | 10 tid | | | |
| ? Aspirin | | | 2.5 gr spd | | | |
| ? Low fat diet | | | | | | |
| ? Exercise program | | ▲ | | | | |
| Asthma | | ▶ | | Doing better... | Pt learned s... | Pt with long... |
| Right Breast carcinoma | | | | | . Normal ch | |
| Vital signs | | | | | | |
| Pulse | | | | 80 | 92 | 72 |
| Respiration | | | | 16 | 18 | 16 |
| Weight(kg) | | | | 84.5 | 84.7 | 84.3 |
| Chest PA and Lateral | | | | | | |
| Beclovent | | | | 2 puffs q4-6 | 2 puffs q4-6 | 2 puffs q4-6 |
| Seldane | | | | 60 mg bid | 60 mg bid | 60 mg bid |

Verify (label for upper section)
Problem (label for Asthma/Right Breast carcinoma section)
Procedure (label for Chest PA and Lateral)
Therapy (label for Beclovent/Seldane)

FIG. 4

COLLAPSIBLE FLOWSHEET FOR DISPLAYING PATIENT INFORMATION IN AN ELECTRONIC MEDICAL RECORD

COPYRIGHT NOTICE

A portion of the disclosure of this patent document contains material which is subject to copyright protection. The copyright owner has no objection to the xerographic reproduction by anyone of the patent document or the patent disclosure in exactly the form it appears in the Patent and Trademark Office patent file or records, but otherwise reserves all copyright rights whatsoever.

BACKGROUND OF THE INVENTION

The present invention relates to the field of user interfaces. More specifically, one embodiment of the invention provides an improved user interface for use by a health care provider in maintaining and viewing information from an electronic medical record.

Health information technology expenditures were estimated to be over $8.5 billion in 1994. Most of these expenses were for financial and administrative systems in hospitals, ancillary department systems, claims processing, and physician office practice management systems. Despite the desirability of integrating multiple systems through a electronic medical record (EMR), there has been only limited and isolated success in automating the most basic and essential clinical function, the physician's chart. With a clear need for rapid and efficient information processing, and a mandate to measure and improve health outcomes, the usefulness of a computerized patient record, based around a physician-accepted clinical workstation, is considerable.

The need for an EMR, while apparent, has heretofore met with great opposition from physicians and lack of success on the part of EMR system vendors. Although the EMR is widely discussed and touted as a near-term certainty, until physicians utilize a workstation as their primary mode of clinical communication, for both display and input, the full potential of the EMR will not be realized. Unfortunately, few physicians are willing to substitute a computer for their current dictated or manual records because they are too cumbersome to use. Consequently, health care organizations cannot get their physicians to use computers for their daily activities of reviewing and collecting patient information. Even where organizations have been successful in introducing computers into physician-patient interactions (often through heroic efforts), the goals of these systems have not been directed toward solving both the physicians' need for better clinical information and the organization's need to change physician practice patterns.

Therefore, what is needed is an easy-to-use and intuitive interface for quickly providing relevant information to a health care provider and filtering out the irrelevant information until it is needed.

SUMMARY OF THE INVENTION

In one embodiment, a user interface presents patient data on a computer display to a health care provider as a flowsheet including an array of category labels with indications of whether the category is in a collapsed state or an expanded state, the collapsed state being a state wherein data items in that category which are tagged as being hidden items are not displayed and the expanded state being a state wherein data items in that category which are tagged as being hidden items are displayed. Also included is a hierarchical structure of data items associated with at least some of the category labels, wherein a parent data item has at least one related data item lower in the hierarchical structure and related data items include child data items. Child items are typically more detailed data regarding the parent item. Child items, themselves, can be parents to their own children showing further detail. For each parent data item, a "zipper" indicator is provided to indicate whether the parent data item is in a "zipped" state or an "unzipped" state, the zipped state being a state where child data items of that parent are not displayed and the unzipped state being a state where child data items are displayed below the parent data item. Thus, within each category of patient information, data items may be hidden or shown and for each data item that is shown, its children may be hidden (zipped) or shown (unzipped).

The display according to the present invention provides a number of advantages to the health care provider user. The first advantage is that the key patient information required for a given encounter can be summarized on a single display screen with the use of intelligent software logic. The second advantage is that any other information in the patient record not visible on the summary view can become immediately visible by expanding a category and/or unzipping a data item to reveal the hidden data items. All of this occurs without the user leaving the single display view. The intelligent software logic used to determine the data items contained in the summary view, and the relation of child to parent data items is provided, in part, through the use of software agents herein referred to as "KnowMeds." These KnowMeds represent the learned pattern of display and input of each physician in a particular clinical context. KnowMeds are discussed below. They are not required for the operation of the collapsible flowsheet, however, they enhance its utility.

In addition to the expansion and collapsing of the data items which represent the rows of the flowsheet, the display also can expand and collapse the columns of the flowsheet which represent the individual encounters between the patient and the provider organization in chronological or reverse chronological order. In the collapsed view, only certain encounters are visible with the corresponding data related to the data items in the rows. In the expanded view, all encounters are visible.

A further understanding of the nature and advantages of the inventions herein may be realized by reference to the remaining portions of the specification and the attached drawings.

BRIEF DESCRIPTION OF THE DRAWINGS

FIG. 1 is a screen view of a display according to the present invention.

FIG. 2 is a second screen view of a display according to the present invention demonstrating some of the operations of the collapsible flowsheet.

FIG. 3 is a screen view of a display according to the present invention showing observation column expansion.

FIG. 4 is a screen view of a display according to the present invention showing a New Problem KnowMed.

DESCRIPTION OF THE PREFERRED EMBODIMENTS

Figure 1:
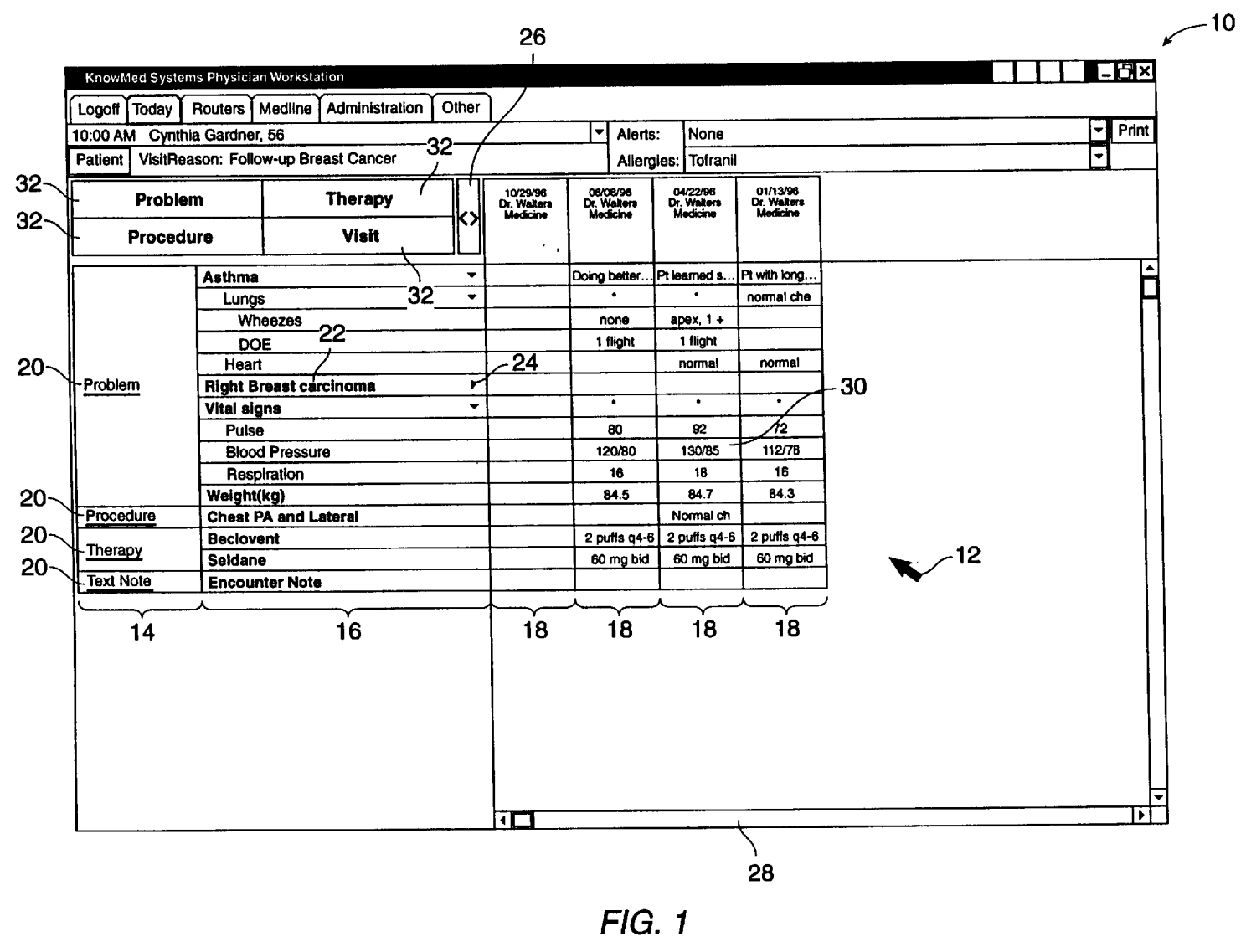

FIG. 1 is a first example of a display 10 which is part of a user interface according to the present invention. A user views display 10 and can interact with display 10 by positioning a cursor 12 over a display element or by using a keyboard, as is well known in the art. Display 10 is divided into several sections, such as a category column 14, an item column 16 and one or more observation columns 18. Each category in category column 14 has a category label 20 identifying the category and each data item in item column 16 has an item label 22 identifying the data item. The data items are organized under each category into a hierarchical, or outline, structure with some data items being parent items and some data items being child items. For example, in FIG. 1, "Asthma" is one of the data items in the category "Problem". "Asthma" is the parent term to the children data items "Lungs" and "Heart". "Lungs" in turn, is the parent to its children "Wheezes" and "DOE". Each observation column 18 has a value box associated with each data item although some might be blank or unused.

Each parent item includes a zipper icon 24 to indicate that there are children and whether those children are visible (unzipped) or hidden (zipped). In the example shown in FIG. 1, zipper icon 24 next to "Right Breast carcinoma" is a right pointing arrowhead indicating that "Right Breast carcinoma" is a parent data item in the zipped position and therefore its children are not visible. Zipper icon 24 next to "Vital Signs" is a downward pointing arrowhead indicating that "Vital Signs" is a parent data item in the unzipped position and therefore its children "Pulse", "Blood Pressure" and "Respiration" are visible. Note that some data items such as "Heart" do not have a zipper item, which means that there are no children of that data item. A user can toggle between the zipped state and the unzipped state for a parent item by positioning cursor 12 over the parent item's zipper icon 24 and clicking a mouse button (or providing any other input selection indication as might be known in the art).

Each category can either be in a collapsed state or an expanded state. In the collapsed state, data items tagged with a "hide" attribute are not shown in item column 16. Data items can either be tagged with a "hide" attribute or its opposite, the "show" attribute. In the embodiment shown in the figures, hidden data items are indicated (when shown) by italicized text and shown data items are indicated by normal text. The collapsed state of a category is indicated by its category label 20 being shown in underline font, whereas the expanded state is indicated by its category label 20 being shown italicized. Since all of the categories shown in FIG. 1 are collapsed, no hidden data items are displayed.

FIG. 2, however, shows the result of the user having performed three operations while viewing FIG. 1. The user clicked on the "Therapy" category label 20, the label changed from underline font to italics font and the hidden data items are displayed ("AC Regimen" and "Tamoxifen"). The user also clicked on the zipper icon for "Right Breast Carcinoma" to unzip it and show its children, and clicked on the zipper icon of "Vital Signs" to zip it and hide its children.

Referring again to FIG. 1, several observation columns 18 are shown. An observation column 18 corresponds to a patient encounter, such as a physician visit, telephone call, hospitalization, home visit or any other type of encounter. Generally, observation columns 18 are ordered by date, with the oldest one being on the right and the newest one (for a current encounter) being on the left. Using an expansion button 26, the user can toggle between an expanded column view and a collapsed column view. In the expanded column view, columns for each of the encounters are shown. If they are not all visible, the user can use a horizonal scroll bar 28 to scroll through observation columns 18. In the collapsed view, only those encounters for the current health care provider user are shown. The current health care provider is determined in a log-in process. In alternate embodiments, the criteria for filtering columns might be different than filtering by the current health care provider.

Figure 3:
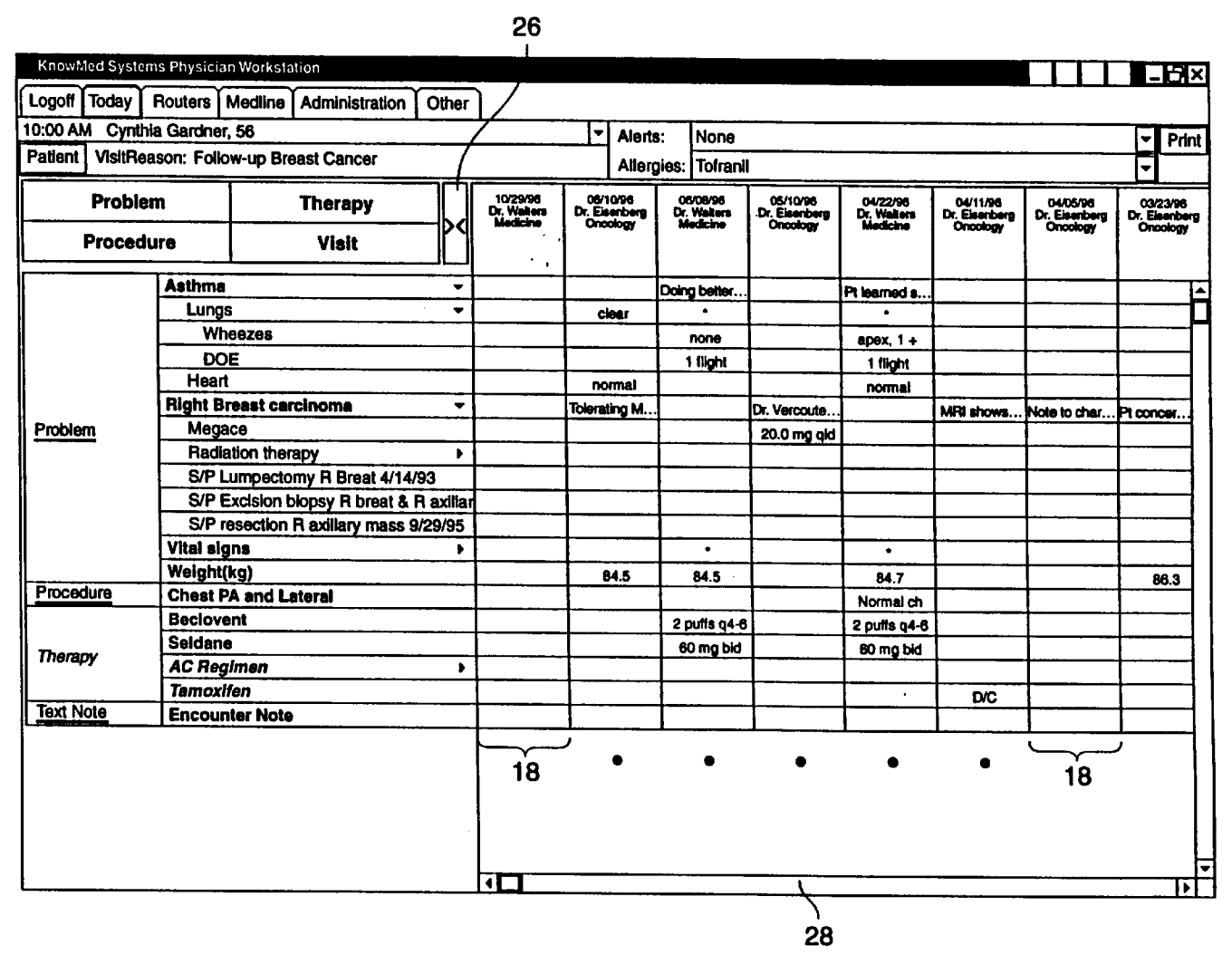

FIG. 3 shows the effect on observation columns 18 after the expansion button 26 in FIG. 2 is pressed. This caused all of the hidden encounters to Dr. Eisenberg to become visible. The legend on expansion button 26 changes from "<>" to "><" indicating that pressing expansion button 26 again will reverse the expansion. In some embodiments, another type of observation column expansion and collapse is provided wherein multiple encounters are grouped in a single column. The display choices would then be to show each encounter as a separate column or only show a summary of the multiple grouped encounters in the column.

Within each observation column 18 are the observation values, such as observation value 30 in FIG. 1, corresponding to the data item label for that row For example, FIG. 1 shows that during an encounter on Apr. 22, 1996, the patient had a blood pressure of 130/85. Not all data items need have values for each encounter.

Data items can be added to the existing data items by selection using item buttons 32 shown in FIG. 1. Clicking on an item button 32 provides the user with a list of items for the selected category which can be added. The "Problem" category contains data items relating to diagnoses, symptoms, signs, and the like. The "Procedure" category contains data items relating to laboratory tests, X-rays and other procedures. The "Therapy" category contains data items relating to medications, diets and the like. For longer notes such as discharge summaries, history and physicals, operative reports and the like, the "Text Note" category is used.

In addition to changing the zipper states and the category states, the user can change the show/hide tag for a data item. In a particular embodiment, this is done by dragging an item label 22 leftwards over its category label 20 and dropping the item label within the screen area in category column 14 for that category. The parent-child relationships between data items can also be changed by the user by simply dragging the data items around within item column 16. To make a data item a child of another data item, it is dragged to a position just below and indented under that data item and dropped there. To remove a data item as a child in order to make it an independent term equal in hierarchy to its parent, the data item is dragged to the left so that it is no longer indented.

In a specific implementation, the user interface is part of an electronic medical records (EMR) system running on a personal computer or workstation under the Windows 95 operating system using an object-oriented development environment including programs written in C++ and Smalltalk, however other development environments can be used.

KNOWMEDS

A "KnowMed" is a term used to describe a medical knowbot. A "knowbot" is a "knowledge robot" or software agent which can be "trained" or configured to filter large amounts of available data and present only data considered relevant to an individual user. Thus, a KnowMed is a software agent acting on behalf of a user to determine which data from among the large EMR database of a patient should be displayed and in what format. Of course, depending on its training, the KnowMed might also be acting on behalf of the organization to which the user belongs as well.

Two main types of KnowMeds are described here: "Chartview" KnowMeds and "New Problem KnowMeds."

Each user who has a log-in account with the system has an associated Chartview KnowMed acting on his/her behalf to determine the content and format of the display described above. Thus, the Chartview KnowMed enhances display 10 and makes it more effective. Of course, display 10 can be used without any KnowMeds and still be useful to the user and, likewise, the KnowMed concept could be applied to other user interfaces and display and navigation models.

The Chartview KnowMed uses pattern recognition logic to "learn" the preferred format of data displayed in display 10 so that a default view of a patient record can be presented without requiring user configuration. When first presented with a patient and a user, a fully configured Chartview KnowMed will set up the display elements (categories, data items, observation columns, etc.) and their states and tags according to criteria specific to that user and that patient, such as:

1. Certain data item tags default to hide or show in each category.
2. What data items are children of what parent data items.
3. Whether a parent is zipped or unzipped.
4. Showing medications in the Therapy category or as children of their corresponding Problem.
5. Other default selections.

Criteria #1 might be used, for example, if the user habitually hides inactive medications. Criteria #2 might be set when a user repeatedly places certain data items as child items of other data items. In response, the Chartview KnowMed will default to this in the future. Criteria #3 might be set when a user repeatedly zips or unzips particular data items. For example, if the user habitually zips problems identified by other users, the Chartview KnowMed will default to this in the future. Criteria #4 is used to remember a user preference. The pattern recognition logic is a combination of statistical and empirical rules. The simplest form is to look for modal patterns and apply them to future displays.

New Problem KnowMeds are slightly different, in that they are invoked when the user adds a new diagnosis, symptom or sign to a patient's record. The new entry is the event which triggers the New Problem KnowMed. Upon selecting the new data item, the system will automatically display data items in a special "Verify" category in addition to the data item selected.

FIG. 4 shows an example of a New Problem KnowMed for the Angina Pectoris. The data items in the Verify category are those which the user has most often added to other patients' records when adding a new diagnosis of Angina Pectoris. The question marks (?) next to each item are to indicate that the user must select each item that s/he wishes to enter into this patient's record. This is done by clicking on the item. The zipped state, hierarchical location, show/hide tag, etc. of these additional items are also determined by the New Problem KnowMed.

The content and format of the data items displayed in the Verify category are determined by the New Problem KnowMed in a similar fashion to the Chartview KnowMed. Its logic tabulates the data items and their formats which were added to the record on the previous occasions when the user added the triggering diagnosis, symptom or sign. Again, the modal behavior will be used unless overridden by an empirical rule.

The above description is illustrative and not restrictive. Many variations of the invention will become apparent to those of skill in the art upon review of this disclosure. Merely by way of example the user interface described above might include a dictation or voice interface in addition to a mouse and keyboard. The scope of the invention should, therefore, be determined not with reference to the above description, but instead should be determined with reference to the appended claims along with their full scope of equivalents.

What is claimed is:

1. A user interface for presenting patient data on a computer display to a health care provider, wherein the computer display is part of a computer system including an input device, the user interface comprising:

an array of category labels, wherein each category label indicates a name for a category of data items;

for each category, an indication of whether the category is in a collapsed state or an expanded state, the collapsed state being a state wherein data items in that category which are tagged as being hidden items are not displayed and the expanded state being a state wherein data items in that category which are tagged as being hidden items are displayed;

for at least some of the category labels, a hierarchical structure of data items associated with the corresponding category label, wherein a parent data item is a data item which comprises at least one related data item lower in the hierarchical structure, wherein the related data item comprises a child data item;

for each parent data item, a zipper indicator for indicating whether the parent data item is in a zipped state or an unzipped state, the zipped state being a state where child data items are not displayed and the unzipped state being a state where child data items are displayed.

2. The user interface of claim 1, wherein the zipper indicator is an icon, the user interface further comprising means for accepting user input from the input device to toggle the zipped state for a parent data item when the health care provider selects the icon using the input device.

3. The user interface of claim 1, wherein category states are indicated by distinct fonts of the category labels, the user interface further comprising means for accepting user input from the input device to toggle the category state when the health care provider selects the category label using the input device.

4. The user interface of claim 1, wherein the columns corresponding to a plurality of patient encounters can be toggled between a first state in which all the patient encounters are visible and a second state in which only a subset of the patient encounters are visible.

5. The user interface of claim 4, further comprising means for summarizing multiple visits in a single column and toggling between a first column view state in which multiple visits are summarized in a single column and a second column view state in which each visit is presented in a separate column.

6. The user interface of claim 1, wherein category states and zipper states of parent data items are initially set according to a set of default rules, the user interface further comprising a knowledge engine for determining the set of default rules based on health care provider preferences and previous interactions with the user interface.

* * * * *